United States Patent [19]

Schlosser et al.

[11] Patent Number: 4,672,105

[45] Date of Patent: Jun. 9, 1987

[54] METHOD FOR PREPARING ESTERS OF ACRYLIC ACID AND METHACRYLIC ACID BY TRANSESTERIFICATION

[75] Inventors: Fritz Schlosser, Darmstadt; Peter J. Arndt, Seehiem-Jugenheim; Manfred Mueller, Rossdorf; Lothar Janssen, Breuberg, all of Fed. Rep. of Germany

[73] Assignee: Rohm GmbH Chemische Fabrik, Darmstadt, Fed. Rep. of Germany

[21] Appl. No.: 745,485

[22] Filed: Jun. 17, 1985

[30] Foreign Application Priority Data

Jun. 26, 1984 [DE] Fed. Rep. of Germany ....... 3423443

[51] Int. Cl.$^4$ ............................................. C07C 67/02
[52] U.S. Cl. .................................................. 560/217
[58] Field of Search ........................................ 560/217

[56] References Cited

U.S. PATENT DOCUMENTS 2,891,990  6/1959  Mulvany et al. .................... 560/217
2,891,991  5/1959  Stewart et al. ...................... 560/217
3,784,578  1/1974  Swodenk et al. ................... 560/217

FOREIGN PATENT DOCUMENTS 2744641  4/1979  Fed. Rep. of Germany .

OTHER PUBLICATIONS

Kirk-Othmer, *Encyclopedia of Chemical Technology*, vol. 8, 2nd Ed. (1966) pp. 356-362.

*Primary Examiner*—Natalie Trousof
*Assistant Examiner*—L. Hendriksen
*Attorney, Agent, or Firm*—Oblon, Fisher, Spivak, McClelland & Maier

[57] ABSTRACT

A method for preparing an ester of (meth)acrylic acid with a polyhydric alcohol comprising, transesterifying a (meth)acrylic acid ester derived from an alcohol of 1-4 carbon atoms with a transesterifying polyhydric alcohol in the presence of at least one metal compound catalyst system, said catalyst system being comprised of compounds A or a combination of compounds A+B, wherein A represents at least one compound of the formula: $Li_nY$, wherein Y is halide, chlorate, carbonate, carboxylate of 1 to 6 carbon atoms, an alkoxide of 1 to 4 carbon atom, hydroxide or oxide and n is 1 or 2, and wherein B is the compound: $CaX_q$, wherein X is oxide or chloride, and q is 1 or 2; with the provision that at least one of the two anionic components Y and X is oxygen-containing.

19 Claims, No Drawings

4,672,105

METHOD FOR PREPARING ESTERS OF ACRYLIC ACID AND METHACRYLIC ACID BY TRANSESTERIFICATION

BACKGROUND OF THE INVENTION

Field of the Invention

The present invention relates to a transesterification method for preparing esters of acrylic acid and methacrylic acid ((meth)acrylic acid) with polyhydric alcohols, using as starting materials the esters of (meth)acrylic acid with alcohols having 1–4 carbon atoms. The starting material esters are available from large scale industrial processes and the reaction is conducted in the presence of metal compounds as catalysts.

Discussion of the Invention

The catalytic action of inorganic bases in many transesterification reactions is known. Thus, in JACS, 77, 194 (1955) the transesterification of methyl methacrylate with tetraethylene glycol in benzene in the presence of sodium hydride is described. The methanol formed is distilled off as a benzene-methanol azeotrope.

Japanese Laid Open Application No. 75-142,513 (Chem. Abstr. 84, 136271f) discloses the transesterification of methyl (meth)acrylate with dialkylaminoalkanol in the presence of calcium hydroxide or calcium oxide.

The catalytic acceleration of the transesterification of methyl methacrylate with, e.g. 2-ethylhexanol, by lithium compounds such as lithium hydride, alkyllithium, phenyllithium, lithium aluminum hydride, lithium borohydride, or alkoxide thereof, lithium salts of organic and inorganic acids, lithium acetylacetonate, lithium oxide, and lithium metal is disclosed in Japanese Laid Open Application No. 79-41,815 (CA 91, 40095v). Particular interest has been shown in the transesterification of lower esters of (meth)acrylic acid with glycidol to form glycidyl esters. The transesterification of methyl methacrylate with glycidol in the presence of alkali hydroxides or alkali carbonates, -sulfides, -polysulfides, or -thiosulfates, lithium halides, or sodium-, potassium-, rubidium-, or cesium iodides is the subject of Japanese Laid Open Application No. 80-94,378 (CA 94, 121290u).

The transesterification of methyl (meth)acrylate with glycidol in the presence of alkali halides, particulary lithium chloride, to yield glycidyl (meth)acrylate, is described in Japanese Laid Open Application No. 80-105,676 (CA 94, 121292w), while Japanese Laid Open Application No. 80-127380 (CA 95, 7026h) discloses the transesterification of lower esters of other organic carboxylic acids with glycidol in the presence of alkali halides, particularly sodium bromide.

In transesterification reactions involving polyhydric alcohols, partially esterified esters can be produced which are often difficult to separate from the reaction system. In addition, with esters of polymerizable acids there is the hazard of polymerization under the conditions of the reaction and/or concurrent and subsequent processing.

Thus the problem has existed of devising means of influencing the transesterification of lower carboxylic acid esters, particularly esters of carboxylic acids which can be polymerized by radical polymerization (e.g., acrylic acid or methacrylic acid), with alcohols which contain more than one OH functional group in the molecule such as 2, 2-di(hydroxymethyl)-1-butanol (TMP, or trimethylolpropane), tetraethylene glycol, and the like, such that the maximum possible degree of transesterification, i.e. high yields with maximally high selectivity can be achieved.

The (meth)acrylic acid esters of polyhydric alcohols are industrially important, e.g. as crosslinking reagents in the polymerization of acrylic resins. For example, (meth)acrylic acid triesters of TMP have proven particularly useful in the manufacture of high grade acrylic optical media. The state of the art gives no indication or hint of the fact that a catalyst system comprised of different components which are individually relatively inactive can have a synergistic action in the above-described transesterification reaction.

It has been found in the investigation leading to the present invention that in a system comprised of lower esters of (meth)acrylic acid and polyhydric alcohols, particularly TMP as the polyhydric alcohol, no advantage is afforded by the use of catalysts which are well known to yield the desired results in the transesterification of (meth)acrylic acid with glycidol. In particular, when calcium oxide is employed as the catalyst, mono- and diesters are observed to be formed, but no triester. Lithium salts such as lithium phosphate, -sulfate, -fluoride, -chloride, -iodide, and -acetate also do not catalyze the transesterification with TMP any better. Even the combination of, e.g., lithium phosphate, sodium chloride, or magnesium chloride, with calcium oxide (weight ratio 1:1) does not give any industrially usable conversion to the triester.

A need therefore continues to exist for an improved method of transesterfying (meth)acrylic acid esters with a polyhydric alcohol to form an ester product of improved yields.

SUMMARY OF THE INVENTION

Accordingly, one object of the present invention is to provide a method of providing transesterified (meth)acrylic acid esters in improved yield from the reaction of a simple (meth)acrylic acid ester with a polyhydric alcohol.

Briefly, this object and other objects of the present invention as hereinafter will become more readily apparent and can be attained in a method of preparing a transesterified (meth)acrylic acid ester product by transesterifying polyhydric alcohol in the presence of at least one metal compound catalyst system, said catalyst system being comprised of compounds A or a combination of compounds A+B, wherein A represents at least one compound of the formula: $Li_nY$, wherein Y is halide, chlorate, carbonate, carboxylate of 1 to 6 carbon atoms, an alkoxide of 1 to 4 carbon atom, hydroxide or oxide and n is 1 or 2, and wherein B is the compound: $CaX_q$, wherein X is oxide or chloride, and q is 1 or 2; with the provision that at least one of the two anionic components Y and X is oxygen-containing.

DETAILED DESCRIPTION OF THE PREFERRED EMBODIMENTS

The starting material for the transesterification reaction of the present invention advantageously is an ester of (meth)acrylic acid with alcohols having 1–4 carbon atoms, which esters are industrially in good supply, particularly esters with alcohols having 1–2 carbon atoms, i.e. the methyl and ethyl esters.

As a rule, the polyhydric alcohol reactant of the invention has 2–12 carbon atoms preferably 3 to 8 carbon atoms, with at least two hydroxyl groups in the molecule and at most one hydroxyl group per carbon atom. Suitable polyols include in particular glycols such as ethanediol, propanediol, 1,3-butanediol, 2,2-dimethyl-1,3-propanediol (neopentyl glycol), hexanediol, and the like. Other alcohols include polyethylene glycol compounds of the formula: $H(OCH_2CH_2)_mOH$, wherein m is a number from 2 to about 250. These compounds such as tetraethylene glycol, and polyethylene glycol have molecular weights between 380 and 9000. Other alcoholic compounds include sulfhydryl compounds such as 3,4-dimercapto-1,6-hexanediol and polyols including triols such as TMP.

In the present transesterification reaction the presence of the lithium-containing component A in the catalyst system is necessary, but it is not obligatory in all cases for the calcium-containing component B to be present.

The subject catalyst system (A+B) is advantageously employed in catalytic amounts, generally 0.01 to 10 wt. %, 0.2 to 5 wt. %, based on the amount of the polyhydric alcohol employed. The amount of component A in the catalyst system A+B is 5-100 wt. %, and the amount of component B is 95-0 wt. %, preferably 1-0.1 wt. %. In particular catalyst component, B may be present in amounts up to 5 wt. % of the catalyst system.

With respect to the amount of catalyst in the reaction system, normally from 0.2-1.5 wt. % of component B along with 0.2-1.5 wt. % of component A is used relative to the amount of the transesterifying alcohol. Preferred amounts of components are 1.5 wt. % of component B and 1.5 wt. % of component A.

Examples of A+B catalyst systems include:
Lithium oxide+Calcium oxide;
Lithium hydroxide+Calcium oxide;
Lithium alkoxide+Calcium oxide;
Lithium carbonate+Calcium oxide;
Lithium acetate+Calcium oxide;
Lithium fluoride+Calcium oxide;
Lithium chloride+Calcium oxide;
Lithium bromide+Calcium oxide;
Lithium iodide+Calcium oxide;
Lithium chlorate+Calcium oxide; and
Lithium methoxide+Calcium chloride.

Alkoxide derivatives of lithium include the methoxide, ethoxide, and t-butoxide compounds. Further, single component A systems of lithium compounds comprise lithium oxide, lithium alkoxide (particularly lithium methoxide), or lithium chlorate. Advantageously, an excess of the (meth)acrylic acid ester is used over that needed to transesterify the hydroxyl groups present in the polyhydric alcohol. In general, a 1.5- to 3-fold excess or 4.5- to 10-fold excess, e.g., a 7.5-fold excess is used over the molar stoichiometric amount. In the case of the polyhydric alcohol: TMP, for example, the amount of (meth)acrylic acid ester used is 2-3 times the stoichiometric amount of alcohol needed.

The use of a solvent along with the other components of the reaction mixture is not generally necessary. However, it is possible to use inert (non-radical-forming) solvents including hydrocarbons such as toluene, cyclohexane, hexane, and heptane. A stabilizer (radical scavenger) is recommended, to inhibit polymerization of the (meth)acrylic esters. For this the usual stabilizers may be used such as hydroquinone compounds, thio compounds, or amines, in the usual amounts of 50-5000 ppm. (See H. Rauch-Puntigam and Th. Voelker, "Acryl- und Methacrylverbindungen", Springer-Verlag, p. 165 (1967)).

Advantageously the reaction temperature employed is above room temperature, preferably in the range of 60°-120° C. If the particularly preferred methyl methacrylate or methyl acrylate reactant is employed as the starting ester, the methanol which is formed during transesterification advantageously may be drawn off in an azeotropic mixture with the (meth)acrylic acid ester at 65°-75° C.

In general the overall reaction times are in the range of 1-20 hr, e.g., 5-20 hr or 6-12 hr, preferably 3-10 hr.

The reaction may be carried out as follows: The polyhydric alcohol, preferably TMP, is charged into a suitable reaction vessel with an excess of the (meth)acrylic acid ester and the stabilizer. The catalyst may be added during the reaction or may be present initially. Thus, e.g., lithium alcoholate may be added in a suitable solvent such as lithium methoxide in methanol. It is recommended that the catalyst be added either in solution or in finely divided, mixed form such as a powder or granulate.

The reaction mixture is brought to the reaction temperature with agitation. When methyl methacrylate is used as the starting ester, for example, the mixture is heated to boiling. The resulting methanol is first advantageously drawn off along with unreacted ester at a distillation head temperature of up to 70° C. At a head temperature of up to c. 98° C. the residual methanol is drawn off along with some more of the residual unconverted ester. Finally, the remaining residual unconverted ester is distilled off at reduced pressure at a maximum bottom temperature of 150° C.

Further processing proceeds in known fashion. Thus, it has proved successful to add fuller's earth or activated charcoal to the raw ester product, allow the additive to settle, and then to stir the mixture briefly. Finally, the solid is removed in a settling filter or a pressure filter.

The yield of the desired fully esterified transesterification product is quite high, normally on the order of >90%. Particularly noteworthy is the extremely small proportion of only partially esterified polyols and of additional products to the vinyl double bond which are present in the reaction mixture as byproducts.

Having generally described this invention, a further understanding can be obtained by reference to certain specific examples which are provided herein for purposes of illustration only and are not intended to be limiting unless otherwise specified.

EXAMPLE 1

1800 g Methyl methacrylate, 300 g 2,2-di(hydroxymethyl)-1-butanol (TMP), 0.44 g hydroquinone monomethyl ether (polymerization inhibitor), and 11 g lithium chloride and 33 g calcium oxide as the catalyst system were charged into a four-necked flask provided with a stirrer, a thermometer, an air inlet tube, and a distillation column packed with glass raschig rings. The reaction mixture was heated to 91° C. and an azeotropic mixture of methanol and methyl methacrylate was distilled off through the column at a head temperature of 67°-75° C. After about 3 hr, the transesterification (alcoholysis) was completed, and the temperature in the bottoms of the reaction mixture reached 122° C. The remaining excess methyl methacrylate was distilled off at a bottoms temperature up to a maximum of 150° C. and head temperature 98° C.

After cooling and addition of 0.5% kieselguhr as a filter aid, the residual mixture was filtered. The ester thus obtained contained 98.7 wt. % TMP trimethacrylate and only traces of the di- and monomethacrylate.

EXAMPLE 2

1800 g Methyl methacrylate, 402 g 2,2-di(hydroxymethyl)1-butanol (TMP), 0.44 g hydroquinone monomethyl ether (polymerization inhibitor), and 10 g lithium oxide as the catalyst were reacted according to the method and with the apparatus described in Example 1. The duration of the transesterification reaction was 3.25 hr. The filtered ester contained 90.3 wt. % TMP trimethacrylate, c. 1 % TMP dimethacrylate, and c. 7.5 wt. % Michael adduct as a high-boiling component.

EXAMPLES 3–10

The procedure is as described in Example 1, except that instead of the catalyst comprising lithium chloride and calcium oxide, the catalysts shown in the table below were employed.

| Example No. | Catalyst | Yield of crude (TMP) trimethacrylate (%) | amount of catalyst |
|---|---|---|---|
| 3 | Li—acetate/CaO | 90.7 | 1,5/1,5 |
| 4 | Li—hydroxide/CaO | 93.9 | 0,02/0,08 |
| 5 | Li—oxide/CaO | 94.5 | 0,02/0,5 |
| 6 | Li—iodide/CaO | 95.1 | 1,5/1,5 |
| 7 | Li—methoxide/CaCl$_2$ | 97.2 | 0,05/1,5 |
| 8 | Li—methoxide | 79.2 | 0,005 |
| 9 | Li—chlorate | 92.8 | 1,0 |
| 10 | Li—amide | 86.9 | 0,1 |

EXAMPLES 11–25

(Comparison Examples)

The procedure as described in Example 1 was repeated, except that instead of the catalyst comprising lithium chloride and calcium oxide, the catalysts shown in the table below were employed.

| Example No. | Catalyst | Example No. | Catalyst |
|---|---|---|---|
| 11 | Li—phosphate | 19 | Dibutyltin oxide |
| 12 | Li—sulfate | 20 | Dibutyltin dimethoxide |
| 13 | Li—chloride | 21 | LiCl/Dibutyltin oxide |
| 14 | Li—iodide | 22 | NaCl/CaO |
| 15 | Li—fluoride | 23 | SnCl$_2$/Dibutyltin oxide |
| 16 | Li—acetate | 24 | LiCl/MgO |
| 17 | Mg—methoxide | 25 | LiCl/Al$_2$O$_3$ |
| 18 | Ca—chloride | | |

In none of Examples 11–25 was there any appreciable conversion to (meth)acrylic acid ester product.

EXAMPLES 26–29

The procedure as described in Example 1 was repeated, except that instead of the catalyst comprising lithium chloride and calcium oxide, the following catalysts were employed, some of which catalysts gave high conversions to 2,2-di(hydroxymethyl)-1-butanol (TMP) mono- and dimethacrylate:

| Example | Catalyst | Alcohol | Mono-ester % | Di-ester % | Tri-ester % |
|---|---|---|---|---|---|
| 26 | Li$_3$PO$_4$/CaO | 37.8% | 50.8 | 9.9 | — |
| 27 | CaO | 27.2% | 53.5 | 17.5 | — |
| 28 | LiF/CaO | — | 21.3 | 64.6 | 9.4 |
| 29 | MgCl$_2$/CaO | — | 18.7 | 74.9 | 3.5 |

(Percentages given are wt. % of the residual mixture after the concentration steps as described.)

Having now fully described the invention, it will be apparent to one of ordinary skill in the art that many changes and modifications can be made thereto without departing from the spirit of the invention as set forth herein.

What is claimed as new and is intended to be secured by Letters Patent is:

1. A method for preparing an ester of (meth)acrylic acid with a polyhydric alcohol, comprising trans-esterifiying a (meth)acrylic acid ester derived from an alcohol of 1 to 4 atoms with a trans-esterifying polyhydric alcohol in the presence of a catalyst, where the catalyst is LiCl/CaO or LiBr/CaO or LiI/CaO or a mixture thereof.

2. A method for preparing an ester of (meth)acrylic acid with a polyhydric alchol, said method comprising trans-esterifying a (meth)acrylic acid ester derived from an alchol of 1 to 4 carbon atoms with a trans-esterifying polyhydride alcohol in the presence of a catalyst, where the catalyst is LiCl/CaO or LiBr/CaO or LiI/CaO or a mixture thereof, and wherein the sid trans-esterification is run in the presence of a polymerization inhibiting stabilizer used in an amount of 50 to 5000 ppm.

3. A method of preparing an ester of (meth)acrylic acid with a polyhydric alcohol, said method comprising trans-esterifying a (meth)acrylic acid ester derived from an alcohol of 1 to 4 carbon atoms with a trans-esterifying polyhydric alcohol in the presence of a catalyst, where the catalyst is LiCl/CaO or LiBr/CaO or LiI/CaO or a mixture thereof, with the provision that (i) the catalyst is used in an amount of 0.01 to 10 wt. % based on the amount of polyhydric alcohol used, and (ii) a polymerization inhibiting stabilizer is used in an amount of 50 to 5000 ppm.

4. The method of claim 1, comprising using as the catalyst LiCl/CaO.

5. The method of claim 1, comprising using as the catalyst LiBr/CaO.

6. The method of claim 1, comprising using as the catalyst LiI/CaO.

7. The method of claim 1, comprising using a trans-esterifying polyhydric alcohol containing 2 to 12 carbon atoms, at least two hydroxyl groups, and at most one hydroxyl group per carbon atom.

8. The method of claim 7, comprising using a polyhydric alochol containing 3 to 8 carbon atoms.

9. The method of claim 5, comprising using 2,2-di(hydroxymethyl)-1-butanol.

10. The method of claim 1, comprising running the said trans-esterification reaction for a period of time of 5 to 20 hours.

11. The process of claim 10, comprising running the trans-esterification reaction for a period of time of between 6 and 12 hours.

12. The process of claim 1, comprising using the (meth) acrylic acid ester starting material in an amount which is a stoichiometric excess relative to the polyhydric alcohol.

13. The process of claim 12, comprising using a 4.5 to 10-fold molar excess of starting (meth)acrylic acid ester relative to the amount of the polyhydric alcohol used.

14. The process of claim 13, comprising using a 7.5 molar excess amount of (meth) acrylic acid ester relative to the amount of polyhydric alcohol used.

15. The process of claim 1, comprising running the transesterification reaction at a temperature above 60° C. and up to 120° C.

16. The process of claim 1, comprising using methyl methacrylates.

17. The process of claim 16, comprising azeotropically drawing-off methanol formed during the course of the trans-esterification reaction, said azeotrope containing methanol and methyl methacrylate.

18. The process of claim 1, comprising obtaining a completely esterified polyhydric alcohol in yields of greater than 90% based on the polyhydric alcohol employed.

19. The process of claim 7, comprising using as the polyhydric alochol a polyethylene glycol of the formula: $H(OCH_2CH_2)_mOH$, wherein m is a number of from 2 to 250.

* * * * *